(12) United States Patent
Zimmermann

(10) Patent No.: US 7,486,068 B2
(45) Date of Patent: Feb. 3, 2009

(54) ROTATING HEAD FOR NONDESTRUCTIVE TESTS

(75) Inventor: Bernd Zimmermann, Koblenz (DE)

(73) Assignee: Prueftechnik Dieter Bush AG, Ismaning (DE)

( * ) Notice: Subject to any disclaimer, the term of this patent is extended or adjusted under 35 U.S.C. 154(b) by 30 days.

(21) Appl. No.: 11/613,361

(22) Filed: Dec. 20, 2006

(65) Prior Publication Data

US 2007/0159166 A1   Jul. 12, 2007

(30) Foreign Application Priority Data

Dec. 20, 2005   (DE) .................. 10 2005 061 273

(51) Int. Cl.
- *G01N 27/72*   (2006.01)
- *G01N 27/90*   (2006.01)
- *G01R 33/12*   (2006.01)
- *G01R 15/00*   (2006.01)
- *G01B 7/30*    (2006.01)

(52) U.S. Cl. .................. 324/232; 324/207.25; 324/222; 324/262

(58) Field of Classification Search ............ 324/207.25, 324/222, 225, 228, 232, 237–238, 240, 242, 324/262; 338/32 R, 32 H; 73/514.31, 514.39
See application file for complete search history.

(56) References Cited

U.S. PATENT DOCUMENTS

| 3,029,382 A | 4/1962 | Cochran et al. |
| 3,299,350 A | 1/1967 | Tompkins et al. |
| 5,187,435 A | 2/1993 | Geweke |

FOREIGN PATENT DOCUMENTS

| EP | 0 231 865 A2 | 8/1987 |
| GB | 2 014 317 A | 8/1979 |

*Primary Examiner*—Bot LeDynh
(74) *Attorney, Agent, or Firm*—David S. Safran; Roberts Mlotkowski Safran & Cole, P.C.

(57) ABSTRACT

A rotating head for a device for the nondestructive testing of metallic test specimens has probe carriers, stray flux or eddy current sensors, a coupling ring and elastic coupling elements. In this way, tandem-like, roughly forced coupling of the pivoting motions of the probe carriers is produced.

6 Claims, 3 Drawing Sheets

ROTATING HEAD FOR NONDESTRUCTIVE TESTS

BACKGROUND OF THE INVENTION

1. Field of the Invention

This invention relates to a rotating head for use in a device for nondestructive testing of test materials or test specimens, especially test material in the form of metal articles, for example, of bar-shaped rolled material.

2. Description of Related Art

A similar device is known from European Patent EP 0452433 and corresponding U.S. Pat. No. 5,187,435, which is hereby incorporated by reference to its full extent, for the sake of brevity. This invention is a rotating head for nondestructive eddy current testing of, for example, ferromagnetic pipes, bars and wires, including those which are covered.

SUMMARY OF THE INVENTION

A primary object of this invention is to improve the rotating head of a nondestructive testing device of the initially mentioned type such that economical operation is enabled and improved, and more versatility is achieved for conducting stray flux tests and eddy current tests.

This object is achieved by a rotating head which has elastically acting construction elements for tandem-like, roughly forced coupling of pivoting motions of probe carriers to which stray flux or eddy current sensors are attached, the pivoting motions deflecting the stray flux or eddy current sensors and probe carriers based on eccentric position changes of a specimen being tested.

DETAILED DESCRIPTION OF THE INVENTION

Figure 1:
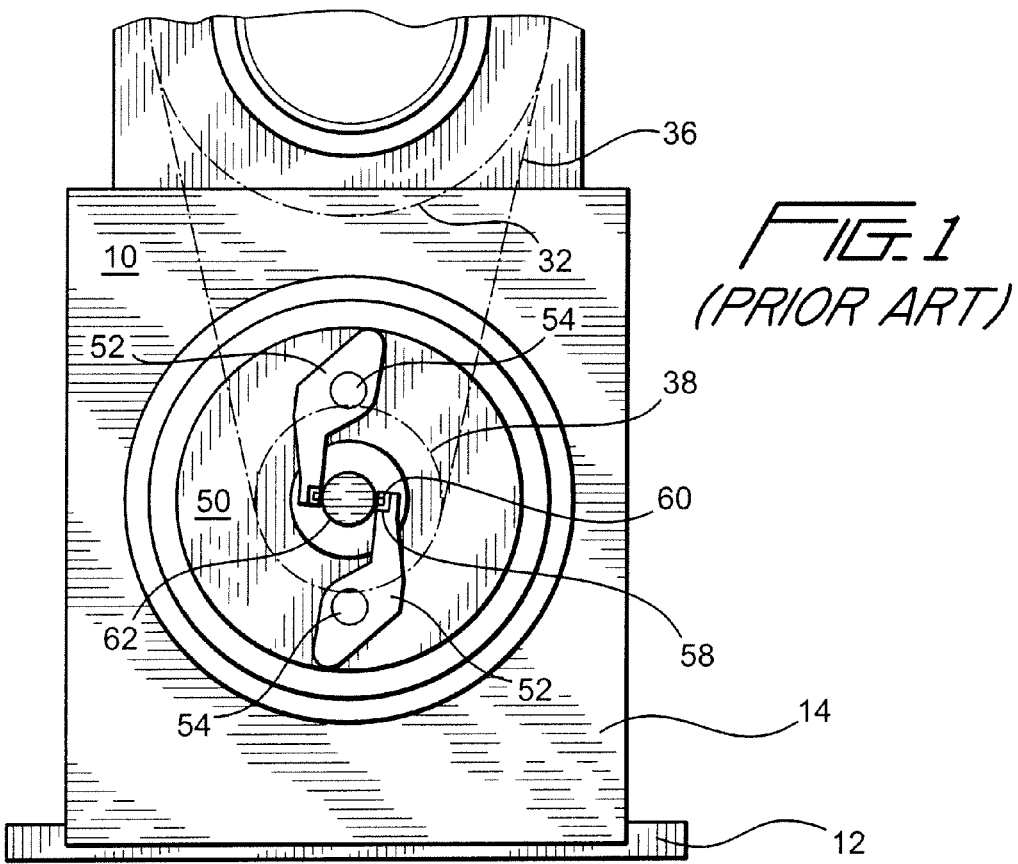
FIG. 1 is an elevational view of the prior art device of European Patent EP 0452443 and corresponding U.S. Pat. No. 5,187,435.

FIG. 1 shows the prior art from the European Patent EP 0452443 and corresponding U.S. Pat. No. 5,187,435. The rotating disk 50 is mounted to be able to rotate relative to the housing 10 together with probe levers 52 which are mounted there and which can be pivoted around pins 54 or the like. The probe levers as sensors which bear eddy current detectors 60 which are mounted here, for example, on probe beams 58 and deliver useful signals.

Figure 2:
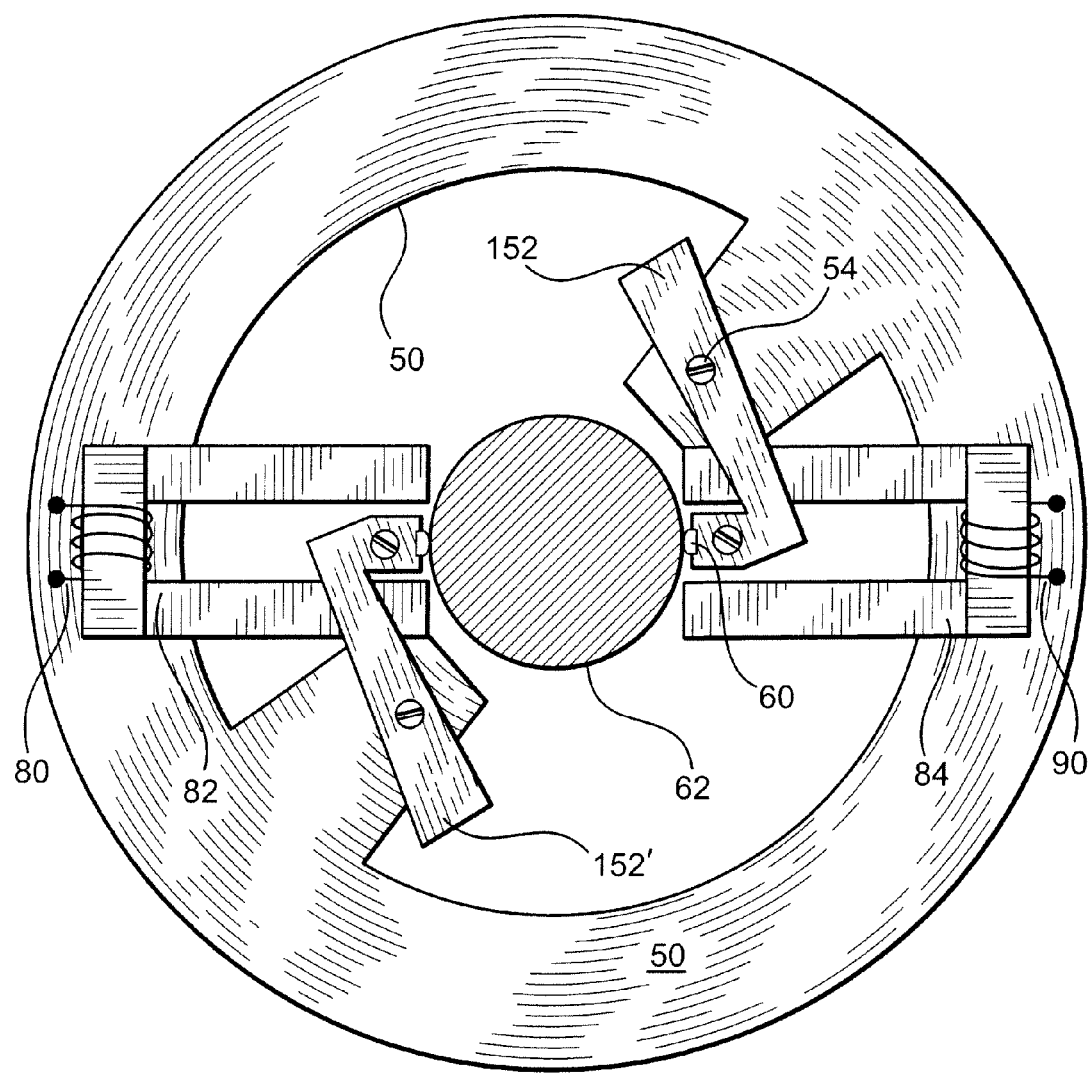
FIG. 2; is a cross-sectional view of construction elements which pivotably move probe carriers and test sensors for use in comparing the prior art device of FIG. 1 with that of the present invention.

A rough approximation of the construction elements of the prior art, if constructed in a manner comparable to that of the present invention, is shown in FIG. 2, the yokes 82, 84 together with exciter coils 80, 90 providing for the test specimen 62 to be magnetized according to the known rotary eddy current test process so that the sensors 60 can detect the eddy current variation which is caused by a material defect of the test piece. Testing with the prior art device can also be performed with stray flux or stationary eddy current transducers in addition to the rotary eddy current transducers.

In accordance with the present invention, it is possible to move the eddy current sensors much closer to the test article than was possible in the past. The reason for this is that the pressure forces of the sensors acting against the test article can be kept much smaller than has been or could be provided in the past. Therefore, for this reason, there can also be an eddy current sensor which functions with a rather low contact force on the test article (instead of the previously necessary contactless sensors). As a result, higher signal frequencies can be detected, or what is equivalent, defects with smaller dimensions on the test specimen than was possible in the past.

Figure 4:
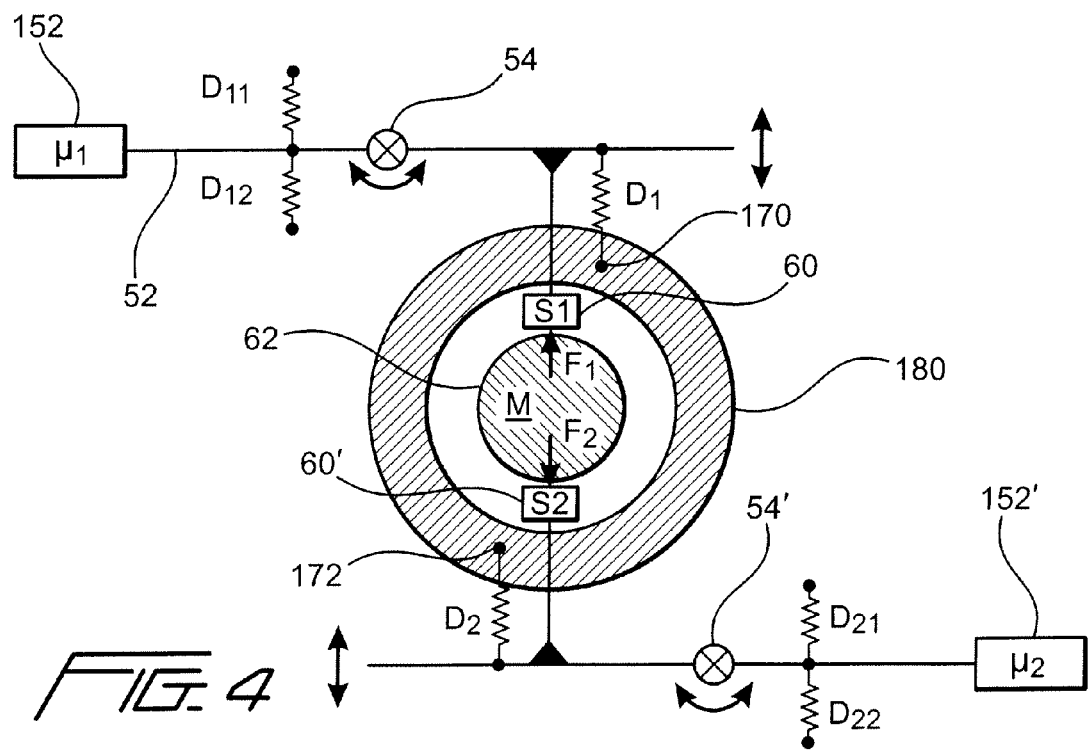
FIG. 4 is schematic representation for explaining how movement of the sensors is elastically controlled based on eccentric position changes of the test specimen.
Figure 3:
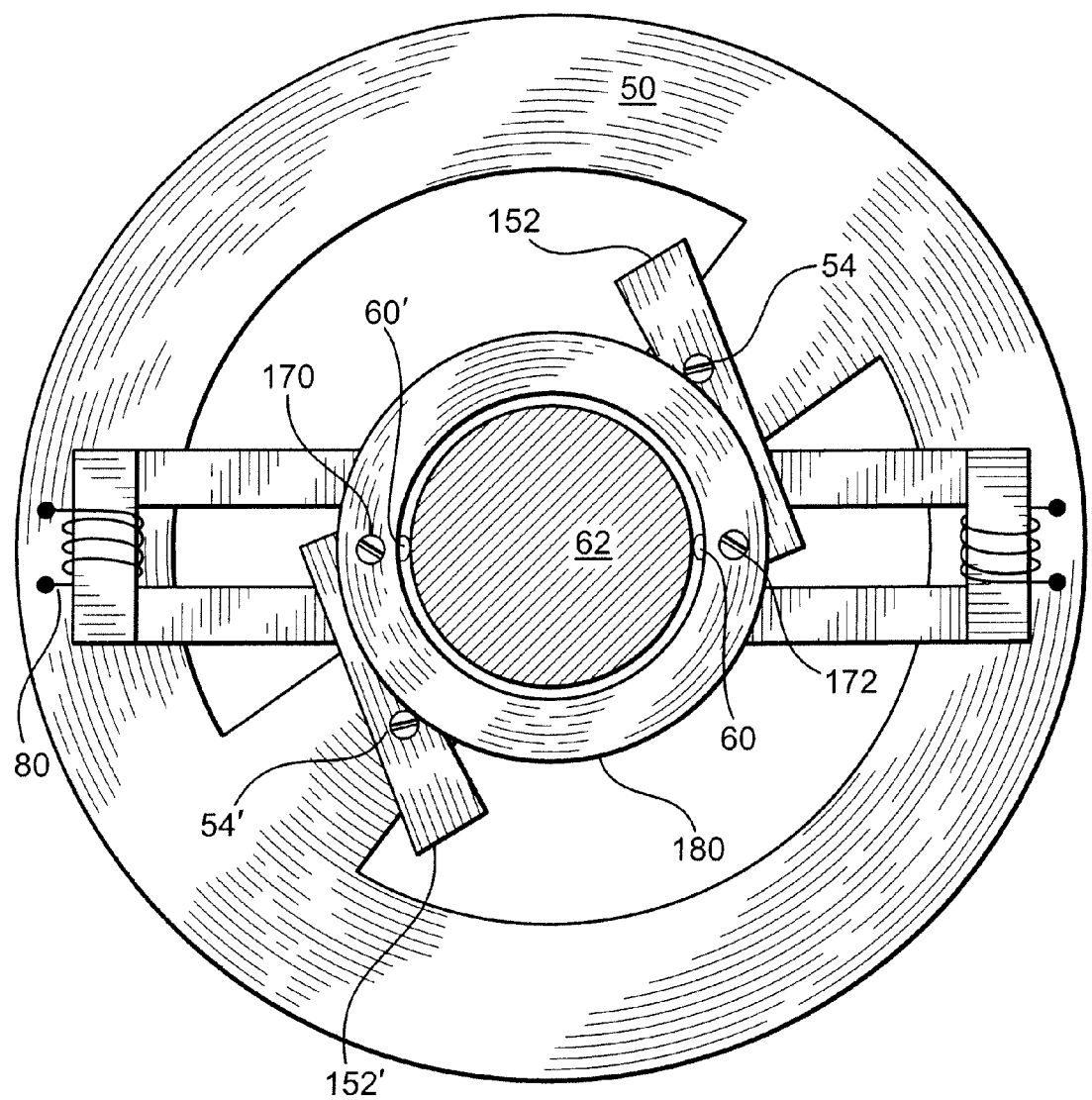
FIG. 3 is a cross-sectional view corresponding to that of FIG. 2, but showing construction elements which pivotably move probe carriers and test sensors attached thereto in accordance with the present invention.

The actual innovation in accordance with the invention is apparent from FIGS. 3 & 4.

As is apparent from FIG. 3, the probe levers 152, 152', which can be pivoted around the bearing elements (for example, pins) 54, 54', have their motion coupled via a coupling ring 180 with interposition of elastic elements (not shown in FIG. 3). For this purpose there are coupling elements 170, 172 which cause the desired elastic coupling of the probe levers 152, 152' to the coupling ring 180. In this way, for example, a pivoting motion of the probe lever 152' to the left, caused by the eccentricity of the test article 62 acting on the contact-making sensor 60', provides for the sensor 60 on the sensor lever 152 to follow this motion in the desired sense without pressure springs, an electromagnetic actuator or the like being necessary. The same applies to a pivoting motion of the probe lever 152 to the right which then applies a tension motion to the probe lever 152' together with its sensor 60' so that two of these sensors remain resting on the test article with a relatively light contact force, always located at least in the immediate vicinity of the test piece. It goes without saying that the inside diameter of the coupling ring 180 must be larger than the outside diameter of the test article 62. The coupling ring 180 is preferably produced from a light, stable material, such as titanium or aluminum, optionally also from a carbon fiber composite.

The conditions illustrated in FIG. 3 are shown in highly schematic form in FIG. 4. Deflection of the sensor S1 (reference number 60) caused by the eccentric location of the test piece 62, e.g., a rod or pipe that is not perfectly strait, and resulting contact force F1 is transmitted almost directly to the coupling ring 180 via an elastically acting construction element D1 which is implemented, for example, in the form of a rubber buffer. The ring acts, for its part, via a second, likewise elastically acting construction element D2 on the sensor lever 152' with a moment of inertia M2. In this way, the sensor lever 152' together with the respective sensor S2 (reference number 60') can follow the receding motion of the test specimen "M" (reference number 62) without spring force. A comparable result applies if contact is made with the sensor S2 and a contact force F2 shifts the sensor S2 so that by means of the elasticities D1, D2 and the coupling ring 180 subsequent displacement of the sensor S1 (60) takes place. Moreover, the elasticities D1, D2 allow matching of the location of the sensors S1, S2 to the test specimen if it should have deviations from its nominal diameter.

In accordance with the invention, it is advantageous to provide additional, possibly selectively acting elastic construction element pairs D11, D12, & D21, D22 which provide for zero positioning (angular position setpoint) of the sensors S1, S2 together with the coupling ring 180 in the absence of the test piece 62.

Altogether, with the innovations in accordance with the invention, it becomes possible with great advantage to be able to sense, i.e., test, the ends of the test piece immediately upon entry into the rotating head; this was not possible with existing methods. Moreover, likewise, with great advantage, an electronically acting distance compensation device which was needed in the past for eddy current sensors can be omitted.

The indicated elastic construction elements can be produced from a metal, or a high-quality rubber-like material, for example, fluorosilicone rubber.

What is claimed is:

1. Rotating head for scanning of the surface of an elongated test specimen, comprising:
   at least two stray flux or eddy current sensors which are attached to pivotally movable probe carriers for contact scanning of the test specimen;
   a coupling ring; and
   elastically acting construction elements;
   wherein the coupling, with interposition of the elastically acting construction elements, provides tandem-like, forced coupling of pivoting motions of the probe carriers and the stray flux or eddy current sensors based on eccentric position changes of the test specimen.

2. Rotating head in accordance with claim 1, wherein additional elastically acting construction elements are provided for setting a specified initial angular position of the sensors.

3. Test device for nondestructive testing of an elongated test specimen, having a housing, a test specimen holder for supporting elongated test specimens during testing, and a rotating head having pivotally movable probe carriers to which at least two stray flux or eddy current sensors are attached for contact scanning of the test specimen;
   wherein the rotating head further comprises:
   a coupling ring; and
   elastically acting construction elements;
   wherein the coupling, with interposition of the elastically acting construction elements, provides tandem-like, forced coupling of pivoting motions of the probe carriers and the stray flux or eddy current sensors based on eccentric position changes of the test specimen.

4. Test device in accordance with claim 3, wherein additional elastically acting construction elements are provided for setting a specified initial angular position of the sensors.

5. Rotating head for scanning of an elongated test specimen, comprising:
   at least two stray flux or eddy current sensors which are attached to pivotally movable probe carriers for contact stray flux or eddy current scanning;
   a coupling ring; and
   elastically acting construction elements;
   wherein additional elastically acting construction elements are provided for setting a specified initial angular position of the sensors prior to placement of an elongated test specimen for scanning, and
   wherein the coupling, with interposition of the elastically acting construction elements, provides tandem-like, forced coupling of pivoting motions of the probe carriers and the stray flux or eddy current sensors, during testing, based on eccentric position changes of the test specimen.

6. Test device for nondestructive testing of an elongated test specimen, having a housing, a test specimen holder for supporting elongated test specimens during testing, and a rotating head having pivotally movable probe carriers to which at least two stray flux or eddy current sensors are attached for stray flux or eddy current contact scanning;
   wherein the rotating head further comprises:
   a coupling ring; and
   elastically acting construction elements;
   wherein additional elastically acting construction elements are provided for setting a specified initial angular position of the sensors prior to placement of a specimen for testing, and
   wherein the coupling, with interposition of the elastically acting construction elements, provides tandem-like, forced coupling of pivoting motions of the probe carriers and the stray flux or eddy current sensors, during testing, based on eccentric position changes of the test specimen.

* * * * *